United States Patent
Hedge et al.

(10) Patent No.: US 7,108,508 B2
(45) Date of Patent: *Sep. 19, 2006

(54) MANIPULABLE DENTAL MODEL SYSTEM FOR FABRICATION OF A DENTAL APPLIANCE

(75) Inventors: Len Hedge, Pleasanton, CA (US); Huafeng Wen, Redwood Shores, CA (US); Srinivas Kaza, Santa Clara, CA (US)

(73) Assignee: Align Technology, Inc., Santa Clara, CA (US)

(*) Notice: Subject to any disclaimer, the term of this patent is extended or adjusted under 35 U.S.C. 154(b) by 454 days.

This patent is subject to a terminal disclaimer.

(21) Appl. No.: 10/446,029

(22) Filed: May 27, 2003

(65) Prior Publication Data

US 2003/0203334 A1    Oct. 30, 2003

Related U.S. Application Data

(63) Continuation-in-part of application No. 10/280,535, filed on Oct. 24, 2002, which is a continuation of application No. 10/087,126, filed on Feb. 28, 2002, now Pat. No. 6,499,997, which is a continuation of application No. 09/779,802, filed on Feb. 7, 2001, now Pat. No. 6,394,801, which is a continuation of application No. 09/454,786, filed on Dec. 3, 1999, now Pat. No. 6,227,851.

(60) Provisional application No. 60/110,868, filed on Dec. 4, 1998.

(51) Int. Cl.
    *A61C 3/00* (2006.01)
(52) U.S. Cl. .............................. 433/53; 433/24

(58) Field of Classification Search ................ 433/6, 433/24, 53, 196, 18, 27, 52, 68, 74, 34; 249/54, 249/55, 155
See application file for complete search history.

(56) References Cited

U.S. PATENT DOCUMENTS

| | | |
|---|---|---|
| 1,831,390 A | 11/1931 | Lindelov et al. ............ 433/74 |
| 2,467,432 A | 4/1949 | Kesling |
| 2,851,728 A | 9/1958 | Spalten et al. |
| 3,660,900 A | 5/1972 | Andrews |
| 3,860,803 A | 1/1975 | Levine |
| 3,916,526 A | 11/1975 | Schudy |
| 3,950,851 A | 4/1976 | Bergersen |
| 3,983,628 A | 10/1976 | Acevedo ............ 433/24 |
| 4,001,938 A | 1/1977 | Cooper |
| 4,014,096 A | 3/1977 | Dellinger |
| 4,022,419 A | 5/1977 | Haker |

(Continued)

FOREIGN PATENT DOCUMENTS

EP    091876 A1    10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—Todd E. Manahan
(74) *Attorney, Agent, or Firm*—Greenberg Traurig LLP

(57) ABSTRACT

A dental appliance fabrication system includes a reconfigurable dental model including a frame having one or more tooth members disposed on the frame; and one or more micro-positioners each coupled to one tooth member to move the tooth in six degrees of freedom relative to the frame.

23 Claims, 10 Drawing Sheets

U.S. PATENT DOCUMENTS

| | | |
|---|---|---|
| 4,160,322 A | 7/1979 | Frazier |
| 4,161,065 A | 7/1979 | Gigante |
| 4,195,046 A | 3/1980 | Kesling |
| 4,324,546 A | 4/1982 | Heitlinger et al. |
| 4,348,178 A | 9/1982 | Kurz |
| 4,478,580 A | 10/1984 | Barrut |
| 4,504,225 A | 3/1985 | Yoshii |
| 4,505,673 A | 3/1985 | Yoshii |
| 4,575,805 A | 3/1986 | Moermann et al. |
| 4,611,288 A | 9/1986 | Duret et al. |
| 4,656,860 A | 4/1987 | Orthuber et al. |
| 4,663,720 A | 5/1987 | Duret et al. |
| 4,671,769 A | 6/1987 | Gill et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | van der Zel |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,163,840 A | 11/1992 | Bourke |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,795,152 A | 8/1998 | Glatt |
| 5,876,199 A | 3/1999 | Bergersen |
| 5,879,158 A | 3/1999 | Doyle et al. ............... 433/24 |
| 5,975,893 A | 11/1999 | Chishti et al. |
| 6,499,997 B1 | 12/2002 | Chishti et al. |

FOREIGN PATENT DOCUMENTS

| | | |
|---|---|---|
| EP | 299490 A2 | 1/1989 |
| EP | 376873 A2 | 7/1990 |
| EP | 490848 B1 | 6/1992 |
| EP | 774933 B1 | 5/1997 |
| EP | 541500 A1 | 6/1998 |
| EP | 731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al., "Laser Electro-Optic System for Rapid Three-Dimensional (3D) Topographic Mapping of Surfaces," *Optical Engineering*, vol. 20(6) (1981), pp. 953-961.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," Program and Abstracts of Papers, Feb. 1975, *Journal of Dental Research*, vol. 54, IADR Abstracts 1979, 2 pages total.

Altschuler, "3D Mapping of Maxillo-Facial Prosthesis," AADR Abstract #607, 1980, 2 pages total..

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.

Baumrind et al., Mapping the Skull in 3-D, Reprinted from The Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug, 26-30, 1975, pp. 1-25.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized diagnosis in Orthodontics for Epidemiological Studies" (progress report), Abstracts of Papers, *Journal of Dental Research*; vol. 71, Special Issue Mar. 1-14, 1992, pp. 28-36.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized analysis of occlusion in the postcanine dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparison with Manual Measurements of Mesio-distal Diameter, Abstract of Papers, 1985, Dept. of Children's Dentistry and Orthodontics, *J Dent Res.*, Mar. 1986, pp. 428-431.

Burstone (interview), "Dr. Charles J. Burstone on The Uses of the Computer in Orthodontic Practice (Parts1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the gnathologic setup and positioner" J. Clin. Orthod., 14:121-133, 1980.

Cottingham, "Gnathologic clear plastic positioner" *Am. J. Orthod.*, 55:23-31, 1969.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), . (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*(Spring 1990) pp. 14-17.

Cureton, "Correcting malaligned mandibular incisors with removable retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

DeFranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 3 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM imaging in dentistry," *Current Opinion in Dentistry*, vol. 1 (1991), pp. 150-154.

Duret, "The Dental CAD/CAM, General Description of the Project," *Hennson International Product Brochure*, Jan. 1986., 18 pages total.

Duret, "Vers une prosthese informatisee," (English translation also attached), *Tonus*, vol. 75, (Nov. 15, 1985), pp. 55-57.

Economides, "The Microcomputer in the Orthodontic Office," *JCO*, (Nov. 1979), pp. 767-772.

Elsasser, "Some observations on the history and uses of the Kesling positioner" *Am. J. Orthod.*, 36:368-374, 1950.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Gim-Alldent Deutschland, "Das DUX System: Die Technik" 4 pages total.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., "Computer Treatment Estimates in Orthodontics and Orthognathic Surgery," *JCO*, (Apr., 1989), pp. 262-28.

Heaven et al., "Computer-based Image Analysis of Artificial Root Surface Caries," "Automated Identification of Landmarks in Cephalometric Radiographs," Abstracts of Papers, *Journal of Dental Research*, vol. 67, Mar. 9-13, 1988, 2 pages total.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kamada et al., "Construction of tooth positioners with LTV vinyl silicone rubber and some case reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling, "Coordinating the predetermined pattern and tooth positioner with conventional treatment" *Am. J. Orthod. Oral. Surg.*, 32:285-293, 1946.

Kesling, "The philosophy of the tooth positioning appliance" *Am. J. Orthod. Oral. Surg.*, 31(6):297-304, 1945.

Kleemann et al., "The speed positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

McNamara et al., *Orthodontic and Orthopedic Treatment in the Mixed Dentition*, Needham Press, Jan. 1993. pp. 347-353.

McNamara et al., "Invisible Retainers", *J. Clinical Orthodontics*, (Aug. 1985) pp. 570-578.

Moermann et al., "Computer Machined Adhesive Porcelain Inlays: Margin Adaptation after Fatigue Stress," IADR Abstract 339, *Journal of Dental Research*, vol. 66(a) (1987), p. 339.

Mörmann et al., "Marginal Adaptation von adhasiven Porzellaninlays in vitro," *Schwizerische Monatsshrift fur Zahnmedizin*, vol. 85 (1985), p. 1118-1129.

Mörmann et al., "Marginale Adaptation von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A new construction of tooth repositioner by LTV vinyl silicone rubber" J. Nihon University School of Dentist, 19(2):93-102, 1977.

Pinkham, "Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz, Invisible Retainers, 59 *Am. J. Orthodontics*, Mar. 1971, pp. 266-272.

Procera Research Projects, *PROCERA Research Projects 1993—Abstract Collection*, 1993, pp. 3-28.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The development of a 3D Cast Analysis System," *British Journal of Orthodontics*, pp. 53-54.

Richmond, "Recording the dental cast in three dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computer Tomography in Maxillofacial Surgical Planning," *Arch Otolamgol Head Neck Surg.* vol. 114 (Apr. 1988), pp. 438-442.

Segu et al., "Computer-aided Cefalometry and New Mechanics in Orthodontics" (Article Summary in English, article in German), *Fortschr. Kieferorthop.* 44, 370-376 (Nr. 5), 1983.

Shilliday, "Minimizing finishing problems with the mini-positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 21 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., Three-Dimensional Analysis of Dental Casts by Means of the Optocom, *J. Dent Res*, Jul.-Aug. 1972, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Varady et al., "Reverse Engineering of Geometric Models—An Introduction," May 13, 1996, pp. 1-28.

Warunek et al., "Clinical use of silicone elastomer appliances" *JCO*, MH (10):694-700, 1989.

Warunek et al., "Physical and mechanical properties of elastomers in orthodontic positioners" *Am. J. Orthod. Dentofac. Orthop.*, 95:388-400, 1989.

Wells, "Application of the positioner appliance in orthodontic treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing,"Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

Web Page Address: http://mfgshop.sandia.gov/1400_ext/1400_ext_Hexapod.htm, Hexapod, Jul. 7, 2000, 2 pgs.

Web Page Address: http://www.parallemic.org/Reviews/Review012p.html , Low-Inertia Parallerl-Kimematics Systems for Submicron Alignment and Handling, Stefan Vorndran—Polytec PI, Inc., Sep. 5, 2002, 9 pgs.

Web Page Address: www. microbotic.dk/artikel_eng.htm, New Robot Technology Crossing the Boundaries of Micro-World Component Handling, Apr. 22, 2002, 3 pgs.

Web Page Address: www.casengineering.com, Six Axis Vibration Isolation System (VIS 6), Aug. 19, 1999, 1 pg.

MANIPULABLE DENTAL MODEL SYSTEM FOR FABRICATION OF A DENTAL APPLIANCE

CROSS-REFERENCES TO RELATED APPLICATIONS

This application is a continuation-in-part of application Ser. No. 10/280,535 filed Oct. 24, 2002; which is a continuation of application Ser. No. 10/087,126 filed Feb. 28, 2002, now issues as U.S. Pat. No. 6,499,997; which is a continuation of application Ser. No. 09/779,802 filed Feb. 07/2001, now issued as U.S. Pat. No. 6,394,801; which is a continuation of application Ser. No. 09/454,786, filed Dec. 03/1999, now U.S. Pat. No. 6,227,851; which claims benefit of Provisional Application No. 60/110,868, filed Dec. 04/1998.

BACKGROUND

The present invention is related generally to the field of orthodontics.

Orthodontic treatments involve repositioning misaligned teeth and improving bite configurations for improved cosmetic appearance and dental function. Repositioning is accomplished by applying gentle controlled forces to the teeth over an extended period of time. Due to the limited space within the oral cavity and extensive movements that some teeth must undergo, the teeth will often be moved throughout a series of intermediate patterns to properly arrange the teeth. For example, molars may be temporarily distalized to create adequate space for movement of the incisors. Thus, a single patient may experience an average of 25–30 stages or alignment patterns before achieving the final desired configuration.

Such repositioning may be accomplished with a variety of orthodontic treatments and dental appliances, including conventional braces, spring retainers, positioners, and other removable aligners. With any treatment, an initial mold of the patient's teeth is made. This mold provides a model of the patient's teeth that the orthodontist uses to formulate a treatment strategy. In some instances, it may be desirable to create additional molds of the patient's teeth throughout the treatment plan to reflect individual stages. For example, the treatment strategy may be re-evaluated or a dental appliance may need to be fit to an intermediate tooth configuration.

The need for intermediate tooth configuration molds is particularly significant when using removable elastic appliances to move the teeth. Such elastic appliances typically include a thin shell of elastic material that generally conforms to the pattern of a patient's teeth, but is slightly out of alignment with the initial tooth configuration. By properly choosing the alternate configuration, placement of the elastic appliance over the teeth will move individual teeth to a desired position. Over time, multiple elastic appliances used in successive stages of treatment, will move the teeth to intermediate or final tooth positions. Such a system is described in U.S. Pat. No. 5,975,893, and in published PCT application WO 98/58596 which designates the United States and which is assigned to the assignee of the present application. Both these documents are incorporated by reference for all purposes. When using elastic appliances as described above, a series of appliances are made to reflect the successive stages of treatment. Such appliances are typically made by heating and vacuum or pressure-sealing a sheet of thermoformable plastic over the dentition of a mold. Traditional methods of dental mold making may be utilized to fabricate a mold for such use. These methods require first forming an impression of the patent's dentition using a suitable impression material, such as alginate or polyvinylsiloxane (PVS). Plaster is then poured into the impression to create a permanent, three-dimensional mold of the dentition. To create an appliance to reflect the next desired tooth configuration in the series of treatment stages, a new mold must be created to reflect the desired configuration. This involves individually cutting the teeth from the mold and resetting the teeth in the desired configuration. Wax is then used to fill in the spaces and represent gingiva. This is a tedious process which compounds both cost and time of treatment for the patient. Resetting is accomplished by either taking into service a laboratory technician or by sending the mold out to a dental laboratory. This process typically requires 2.5 weeks to be accomplished. This represents lost time in the treatment plan as the patient cannot progress to the next stage of treatment until a positioning appliance with the new desired configuration is created. Since such an orthodontic treatment may require, for example, 25 intermediate reset molds to represent 25 stages of treatment progress, the cost and time required for such mold making may be prohibitively high.

The process of iterative mold making may be improved with the use of digital imaging and computer controlled molding systems. Here the patient's initial tooth arrangement and shape of the patient's dental arch are represented by a digital data set. The data set can then be manipulated to reflect progressive tooth arrangements. For each arrangement, the data may be used to guide computerized model fabrication systems to create a corresponding three-dimensional mold. Such techniques may speed production time and reduce costs by eliminating the need for artistic resetting of teeth in mold manufacturing.

Although the above described process aids in the production of iterative molds, further improvement may be desired. The cost in time and materials to produce each mold, though lessened, may still be significant. This cost is additive, as each new stage in treatment or each change in treatment requires the production of a new mold. Likewise, the cost of storing a series of molds for each patient throughout treatment may be formidable. In addition, it may be desirable to visualize a sequence of treatment stages, particularly in an academic environment or in a preliminary patient meeting.

For these reasons, it would be desirable to provide an alternative apparatus and methodology for realizing a series tooth configurations. Such apparatus and methods should be economical, reusable, reduce time consumption, reduce material waste, and, in particular, should reduce the need for fabricating multiple casts of teeth arrangements for stages in the orthodontic treatment. At least some of these objectives, as well as others, are met by the apparatus and methods of the invention described hereinafter.

SUMMARY

The present invention provides a manipulable or reconfigurable dental model system and methods for its use to model a series of tooth configurations corresponding to sequential tooth movements during an orthodontic treatment.

When a patient undergoes orthodontic treatment, teeth and bite configurations are realigned in a series of stages. Each stage represents a new pattern or dental configuration that will eventually lead to a proper final positioning of the entire dentition. Progress from the initial configuration, through the intermediate stages and finally to the final configuration may be accomplished using any one or a combination of different dental appliances. Of particular interest to the present invention, many of these appliances may be made using a dental mold representing the patient's dental configuration. In particular, thermoformable polymeric positioning appliances which fit over the patient's teeth may be formed over a three-dimensional mold of the patient's dentition. When successive appliances are used throughout treatment to reposition the teeth from initial to final configuration, a new mold has typically been produced to fabricate the appliance for each stage.

The present invention provides an apparatus and methods which employ a manipulable or reconfigurable mold to model patient dentition and optionally gingiva at each stage of treatment.

In one embodiment of the present invention, a single dental mold is manipulated and reconfigured to model different tooth configurations by controlling the movement of at least some individual tooth members, or groups of members, with manipulation mechanisms. The tooth members may be composed of any natural or synthetic material which can be formed to represent the teeth and other dental features in the dental model. Generally, the tooth members are supported by or on a frame which is typically configured to a patient's dental arch. The frame provides a support, typically a hollow interior portion in which the tooth members are positioned. The tooth members are coupled individually or in groups to one or more manipulation devices located on or in the support, typically being disposed within the hollow interior portion of the frame. Each manipulation device provides the mechanisms necessary to position and rearrange one or more of the tooth members relative to the frame and to each other. In this way, multiple successive tooth arrangements can be provided using a single mold without having to provide individual casts for each arrangement.

In a preferred embodiment of the present invention, a dental model system is comprised of independently reconfigurable teeth and gingiva to model different tooth configurations with supporting gingiva. The tooth members may be designed and manipulated as described above. The simulated gingiva may be independently manipulated to correspond to the patient's gingiva throughout treatment. The presence of simulated gingiva on the dental mold is necessary for the production of some dental appliances. For example, elastic repositioning appliances are typically formed over the entire dentition and may extend to partially cover the gingiva. After trimming of such appliances, portions of the gingiva may still be covered by the appliance, particularly in the regions between the teeth. Therefore, it is necessary to form the appliance with receptacles to receive the both the patient's teeth and associated gingiva for proper fit. This may be accomplished with simulated gingiva which is integral or independent of the dental mold of the present invention. Likewise, the simulated gingiva may be manipulated independently or jointly with the tooth members.

While the present invention is most advantageously used with only a single reconfigurable dental model system, it will be appreciated that in some cases it may be desirable to employ two or more reconfigurable model systems for a single patient, e.g. when the total tooth movement is greater than that which may be achieved with a single manipulable dental model system. Thus, in some cases, two or more reconfigurable model systems may be used for preparing or modeling multiple sets of tooth moving appliances for a single patient.

After the tooth members and simulated gingiva on the dental mold are configured to a desired position, a dental appliance can be made to fit the dentition. In the case of elastic positioning appliances, a thermoformable polymeric material can be applied to the mold to heat and form the appliance. Alternatively, reaction casting may be used. The mold can then be reconfigured to permit fabrication of the next mold, and the steps repeated until the totality of appliances are produced. The appliances, of course, need not all be produced at the same time. Indeed, it is a particular advantage that the reconfigurable mold may be retained and used at a later date (i.e., after an initial production of appliances).

In the first aspect of the present invention, the reconfigurable model system may be produced with manual mold making methods. First an initial mold of the patient's teeth and dental arch are created. This may be accomplished with traditional mold making methods, such as those described in Graber, Orthodontics: Principle and Practice, Second Edition, Saunders, Philadelphia, 1969, pp. 401–415. The casts may be made from materials, such as plaster, stone, acrylic, urethane, epoxy, plastics, wood, paper, metals, ceramics, porcelain, biomaterials or any material that would provide a stable structure for later processing conditions. The teeth may then be separated from the mold using knives, saws, files or other cutting tools, or the teeth may be cast individually from known methods. The frame may be produced by a variety of methods, including machining, molding, or construction from functional materials. Likewise, the frame may be generated from the mold of the dental arch, by hand-carving, machining or other methods. Appropriate attachment sections for the tooth members may be generated for coupling the members to the manipulation mechanisms.

In a second aspect of the present invention, the reconfigurable model system may be produced with the use of digital imaging and computer controlled molding systems. To create the dental arch and tooth members, a digital data set (hereinafter IDDS) representing a patient's initial tooth arrangement and shape of the patient's dental arch is obtained. The IDDS may be obtained in a variety of ways. For example, the patient's teeth may be scanned or imaged using well known technology, such as X-rays, three-dimensional X-rays, computer-aided tomographic images or data sets, magnetic resonance images, etc. Methods for digitizing such conventional images to produce data sets useful in the present invention are well known and described in the patent and medical literature. Usually, however, the present invention will rely on first obtaining a cast of the patient's teeth by traditional methods as described above. After the casting is obtained, it can be digitally scanned using a conventional laser scanner, destructive scanning or other range acquisition system to produce the IDDS. General techniques for producing plaster casts of teeth and generating digital models using laser scanning techniques are described, for example, in U.S. Pat. No. 5,605,459, the full disclosure of which is incorporated herein by reference.

Once the initial cast of the patient's teeth is made and digitized, a new cast model of the individual patient's teeth may be physically re-created from the IDDS. This may be accomplished with the use of a proprietary software application, commercially known as TREAT, available from Align Technology Inc. of Sunnyvale, Calif. A description of the software is included in U.S. Pat. No. 5,975,893, previously incorporated by reference. With TREAT, a three-dimensional, digital image of the patient's teeth and jaw, including teeth, gingiva and other oral tissue, may be generated from the IDDS data. While viewing the image, the user can virtually delete or cut away any unwanted structure (i.e. data).

The teeth and frame of the reconfigurable model system may be produced with the use of the IDDS data and TREAT software. Individual teeth may be virtually isolated by deleting unwanted sections, such as surrounding gingiva and the base of the originally scanned cast. Optionally, the data can be manipulated, deleted or added to create an attachment section on the tooth to be used for coupling to the manipulation mechanism. The resulting data may then be used to guide model fabrication systems, such as stereolithography, CNC machining, laser machining, and other molding systems, to create molds of the individual tooth members. Similar methodology may be used to produce the frame. In this case, the teeth may be virtually deleted to isolate the dental arch and other desired features. Specific design features in the frame may be created by manipulating, adding or deleting data. The resulting data may then be used to guide molding fabrication systems, such as stereolithography, CNC machining, laser machining, and other molding systems, to create the mold of the frame. In either case, the molded parts may be made from a variety of materials, including but not limited to plaster, stone, acrylic, urethane, epoxy, plastics, wood, paper, metals, ceramics, porcelain or biomaterials, that would provide a stable structure for later processing conditions.

In a third aspect of the present invention, the molded tooth members, generated by any of the above described methods, may be coupled to one or more manipulation mechanisms. The mechanisms are preferably disposed within the frame and are coupled to the tooth members for independently moving each tooth member between a plurality of discrete or continuous positions. The movements may range from one to six degrees of freedom. The movements may be achieved by manual actuation of a mechanism or they may be controlled by a microprocessor in accordance with a software code. Likewise, the movements may be achieved manually with the visual aide of computer graphics. In any case, the tooth members may be manipulated to produce a series of tooth configurations for use in a variety of orthodontic treatments. Such uses may include but are not limited to visualization for educational or descriptive purposes, production of a series of removable elastic positioning appliances, and production of other appliances for dental applications.

In a fourth aspect of the present invention, simulated gingiva may be present and may be manipulated to correspond to the patient's gingiva throughout treatment. Such simulated gingiva may be assembled with the tooth members and frame as an independent body, or it may be integral with the frame. Likewise, it may be manually manipulated or processor controlled. Manual methods may typically involve applying a putty-type material to the frame surrounding the tooth members. Such material may be, but is not limited to, wax, silicone rubber or polysiloxane impression material. Once applied, the putty may be manipulated by hand to model the gingival configuration of the patient. When the dental model system is to be reconfigured, the putty may be partially or entirely removed and reapplied when the tooth members are arranged in the new configuration. Alternatively, the simulated gingiva may be comprised of inflatable bladders or pockets which may be pressure controlled by hand or by a processor. The bladder material may be any elastomeric material, such as nylon, silicone, latex, polyurethane, or the like. The bladders may be present on the frame, surrounding each tooth member. As the bladders are inflated, with air or a suitable liquid, the surface geometry of the simulated gingival layer may be manipulated. In another embodiment, the simulated gingiva may be comprised of a flexible sheeting along the gingival line. Attached to the underside of the sheeting may be a series of support shafts which may be manipulated by hand or by a processor. Such manipulation may alter the surface geometry of the simulated gingival layer.

Additional embodiments of the present invention involve alternative designs and methods of reconfiguring a single dental model system to model different tooth and gingiva configurations. For example, a single model system may be comprised or partially comprised of a series of model shafts which may be manipulated individually or in the groups in the vertical direction by one or more mechanisms. The model shafts may be of any cross-sectional geometry and dimension, and they may have any tip design. In an initial position, the tips of the model shafts may be positioned along a plane parallel to the gingival line. Upon actuation of a mechanism, the model shafts may be raised to varying levels, individually or in groups. Together, the tips of the shafts may form the surface features of the tooth members, gingiva, and other dental features. Different tooth and gingival configurations may be accomplished by movement of the model shafts. In another example, a single dental model system may be reconfigured to model different tooth and gingiva configurations by repeated resurfacing of the original mold. In this case, portions of the original mold may be removed by manual methods, CNC machining, lasers or other material removal methods. Typically, such portions are superficial, allowing the underlying support structure to remain intact. Material may then be added to appropriate portions of the mold by manual methods, stereolithography, or other molding systems. Such resurfacing may be repeated to create different tooth and gingival configurations.

In a further aspect of the present invention, a method is provided for fabrication of a series of dental position adjustment appliances. The method includes providing a dental model system having manipulable tooth members. One or more of the manipulable tooth members is then positioned into a first-tooth arrangement. At this point, a first appliance is formed with an impression from the mold with the teeth arranged in the first-tooth arrangement. After a first appliance is formed, one or more of the manipulable tooth members is positioned in a second-tooth arrangement. A second appliance is then formed with an impression from the mold of the second-tooth arrangement. Additional successive appliances can be formed at the same time and/or at one or more later times.

In an alternative aspect, an improved method for repositioning teeth is provided using appliances comprising polymeric shells having cavities shaped to receive and resiliently reposition teeth. The improvement includes determining at the outset of treatment, a geometry for at least one appliance selected to move the teeth to a desired intermediate arrangement and at a later time (usually after the teeth have been moved through at least one, and usually at least two, three, four, five, or more stages) determining one or more geometries for at least one additional appliance having a geometry selected to move the teeth from an actual intermediate arrangement to a successive intermediate or final tooth arrangement. The actual intermediate tooth arrangement may be determined by any available method, usually by taking a mold and optically scanning the mold, but optionally by direct optical or other scanning of the patient's teeth.

In yet another aspect, a dental appliance fabrication system includes a reconfigurable dental model including a frame having one or more tooth members disposed on the frame; and one or more micro-positioners each respectively coupled to the one or more tooth members to move the tooth members in six degrees of freedom relative to the frame.

Implementation of the above system may include one or more of the following. The micro-positioner has a handle to allow an operator to manually position said tooth member in desired configurations. A computer can deliver computer-generated instructions to said micro-positioner to position said tooth member in desired configurations. An arch-shaped conveyor can move the tooth members to position a different set of tooth members onto the frame. A pick-and-place system can mount each tooth member on the frame, or can mount a set of tooth members on the frame in parallel. The micro-positioner can be a Stewart platform or a hexapod. The micro-positioner can include a movable platform; and a plurality of actuators attached to the movable platform. A plurality of flexures configured to attach each of the plurality of actuators to the movable platform. The actuators are symmetrically attached about the movable platform. A sensor can be configured to sense movement of the micro-positioner and a motion limiter configured to limit the movement of the micro-positioner.

DESCRIPTION

The present invention provides an apparatus and methods to produce and operate a manipulable dental model system to model a series of tooth and gingiva configurations for a single patient throughout orthodontic treatment. The tooth and gingiva configurations represent each stage of treatment from initial presentation, through intermediate stages and to the final desired configuration. The manipulable model system may be used for a variety of purposes, particularly for the production of polymeric and other elastic positioning appliances.

Figure 1:
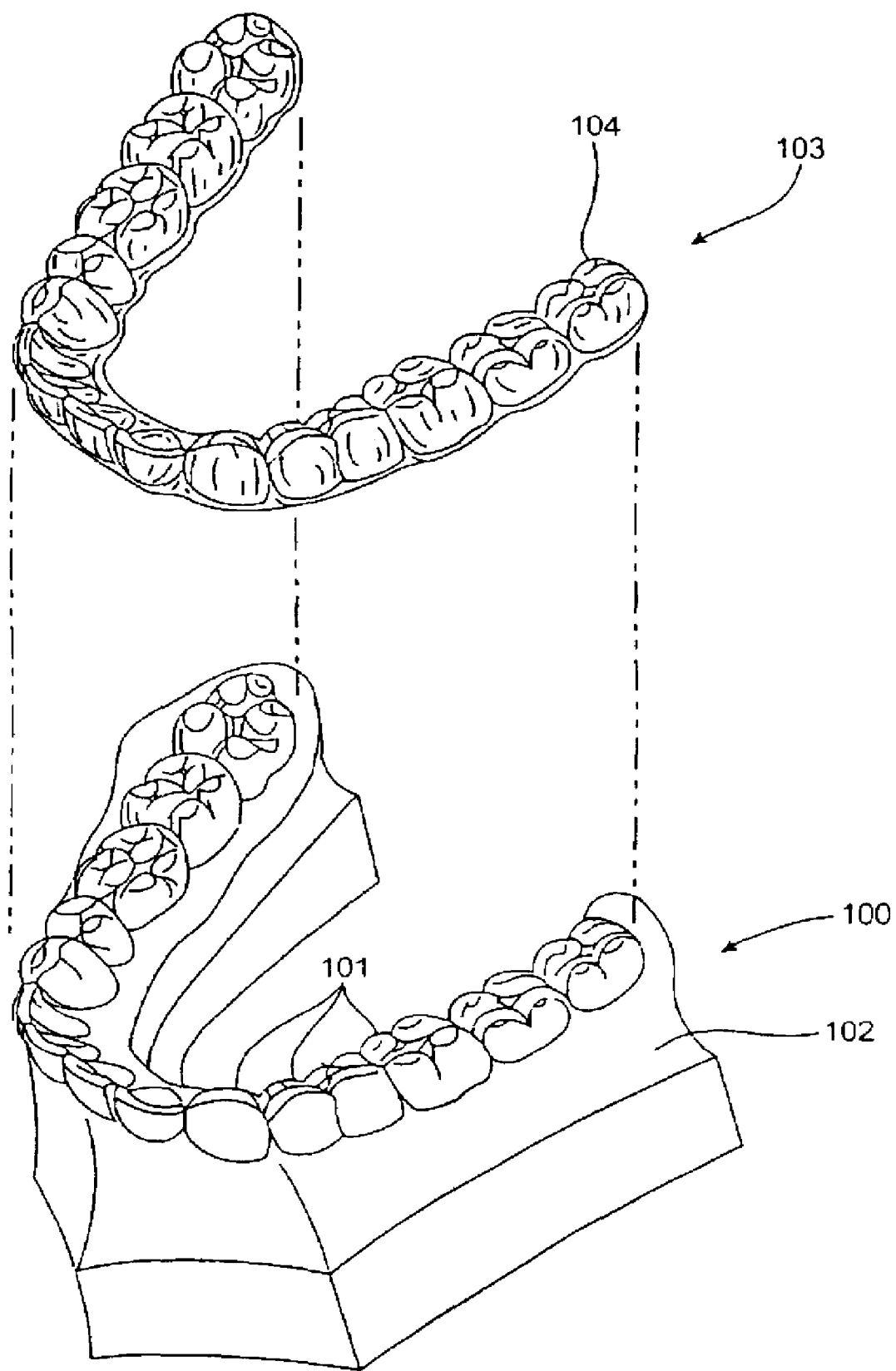
FIG. 1 is a simplified illustration of a reconfigurable dental model system and an elastic positioning appliance fabricated with its use.

In one embodiment of the present invention, a single dental model system is manipulated and reconfigured to model different tooth configurations by controlling the movement of at least some of the individual tooth members, or groups of members, with manipulation mechanisms. Referring to FIG. 1, a simplified illustration of such a manipulable dental mold 100 for the fabrication of dental appliances is shown. In this illustration, the mold 100 is a positive representation of the tooth configuration and dental arch of the lower jaw. The tooth configuration is created by the placement and alignment of tooth members 101. The individual tooth members 101 are typically produced to resemble the individual shape of each of the patient's natural teeth. Although not shown, this may also include any type of dental feature, including but not limited to fillings, caps, crowns, dentures, implants, grafts, and dental appliances. In a preferred embodiment, the tooth members 101 are inserted into ports (not shown) in the frame 102 to support the configuration. It is through these ports that the tooth members may be manipulated.

Also shown in FIG. 1 is an exemplary dental appliance, specifically an elastic positioning appliance 103, which may be produced with use of the mold 100. The appliance 103 comprises a polymeric shell 104 having an inner cavity (not shown) on the underside of the shell 104 which is shaped to receive and resiliently reposition teeth from one tooth arrangement to a successive tooth arrangement. The appliance 103 is preferably formed from a thin sheet of a suitable elastomeric polymer, such as Tru-Tain 0.03 in. thermal forming dental material (Tru-Tain Plastics, Rochester, Minn.), or Essix A-Type or Essix B-Type thermal forming material (Raintree-Essix, New Orleans, La.). The overall method for producing incremental position adjustment is provided in U.S. Pat. No. 5,975,893, previously incorporated by reference. But, in general, the shell 104 is typically produced by heating a thermoformable polymer sheet and vacuum or pressure forming the sheet over the tooth members 101 of the mold 100. Thus, the shell 104 is a direct representation of the characteristics of the mold 100. If this appliance 103 is worn by a patient as a stage in orthodontic repositioning, the shell 104 will preferably, but not necessarily, fit over all teeth or dental features supported by the patient's dental arch. Those teeth which are to be repositioned will be slightly misfit by the appliance to allow force and movement into the desired positions.

Figure 2:
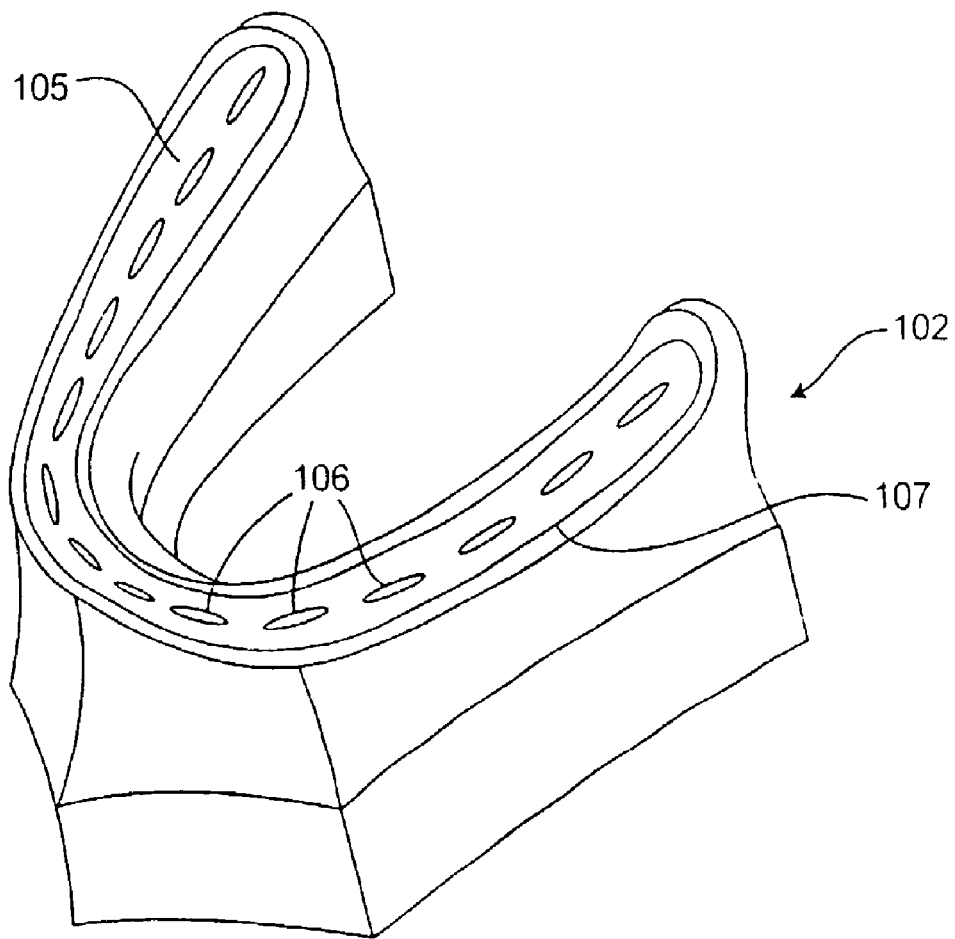
FIG. 2 is a perspective view of an embodiment of the frame of the present invention.

As described, the tooth members 101 are supported by a frame 102, which houses the manipulation mechanisms. A preferred embodiment of the frame 102 is depicted in FIG. 2. The frame 102 is designed to have a hollow interior portion 105 and may include a plurality of ports 106 positioned horizontally along the gingival line 107 at locations which allow for placement of the tooth members 101. The positioning of the ports 106 is meant to correspond generally to the patient's actual or desired tooth positions. The ports 106 are sized such that adequate space is available to avoid interference with the movement of the tooth members 101. Thus, the ports 106 may be oblong or elliptical, as shown, or they may form a variety of shapes, including rectangular, circular, multi-sided and/or multi-curved. Likewise, the ports 106 may be replaced by a continuous channel or track, or the interior portion 105 may not be present, obviating the need for ports.

Figure 3:
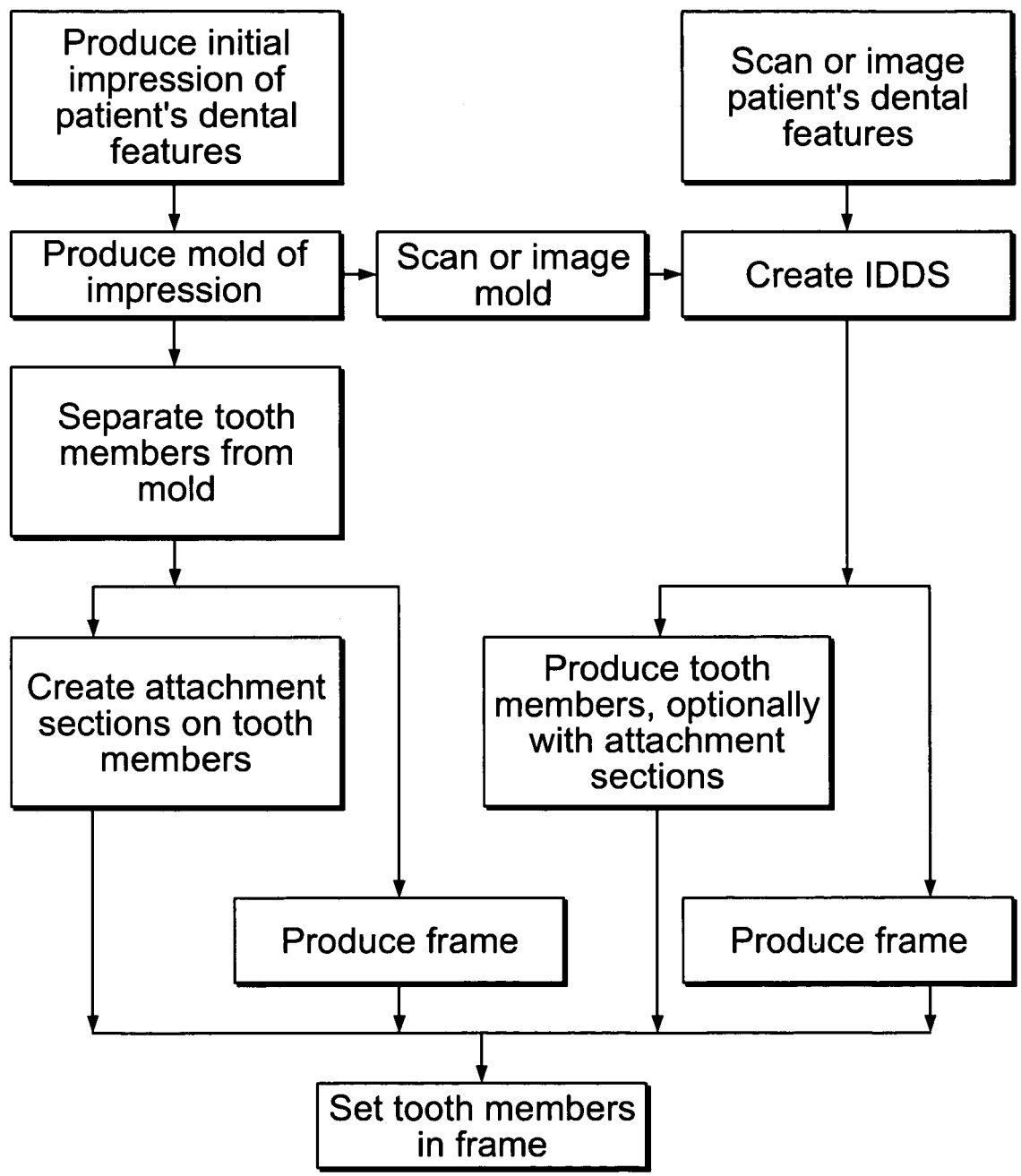
FIG. 3 is a flow diagram of production options for the dental model system.

The tooth members 101 and frame 102 of the dental model system may be produced manually or with the use of digital imaging and computer controlled molding systems, as described previously. These production options are presented in a flowchart, (FIG. 3). Regardless of the production methodology, the resulting components may then be assembled.

Figure 4:
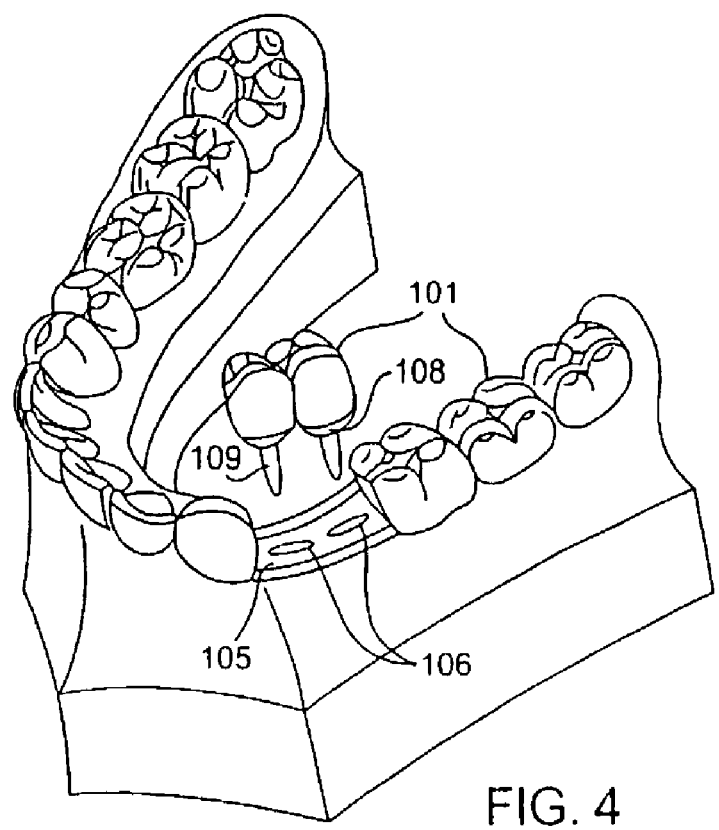
FIG. 4 illustrates an embodiment of arranging the tooth members in the frame by inserting the coupling members through the ports.
Figure 5:
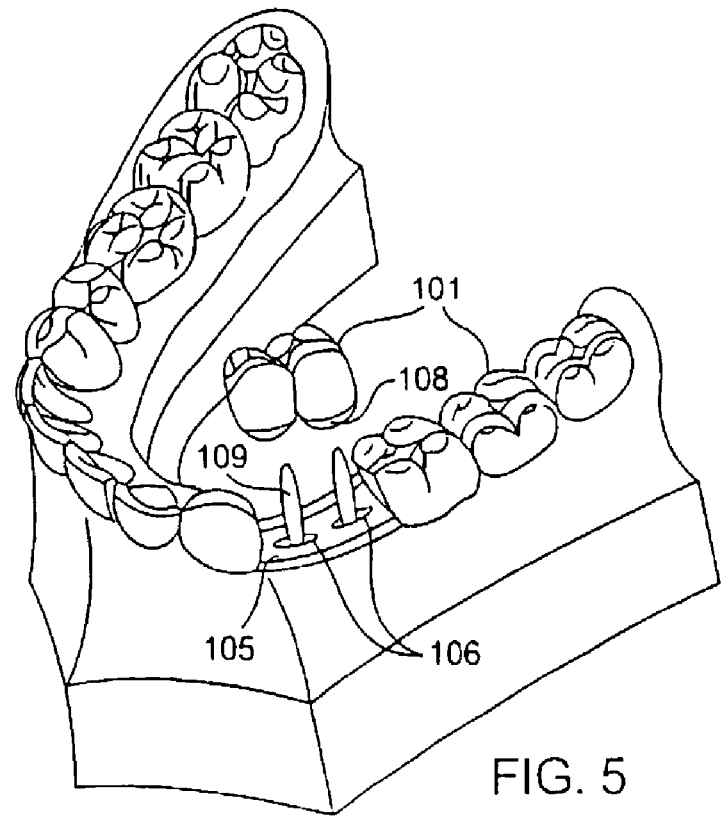
FIG. 5 illustrates an embodiment of arranging the tooth members in the frame by placing the tooth members on coupling members protruding through the ports.

The tooth members 101 may be coupled to one or more manipulation devices by any of a variety of means. Referring to FIG. 4, an attachment section 108 may be present on a bottom portion of the tooth members 101. The attachment sections 108 may be connected to coupling members 109 which may be inserted through the ports 106 for coupling to a manipulation mechanism. Alternatively, referring to FIG. 5, the coupling member 109 may be integral with the manipulation mechanism. In this case, the coupling members 109 may appear as posts or shafts protruding through the ports 106. The tooth members 101 may then be coupled to the coupling member 109 by means of an attachment section 108.

Figure 6:
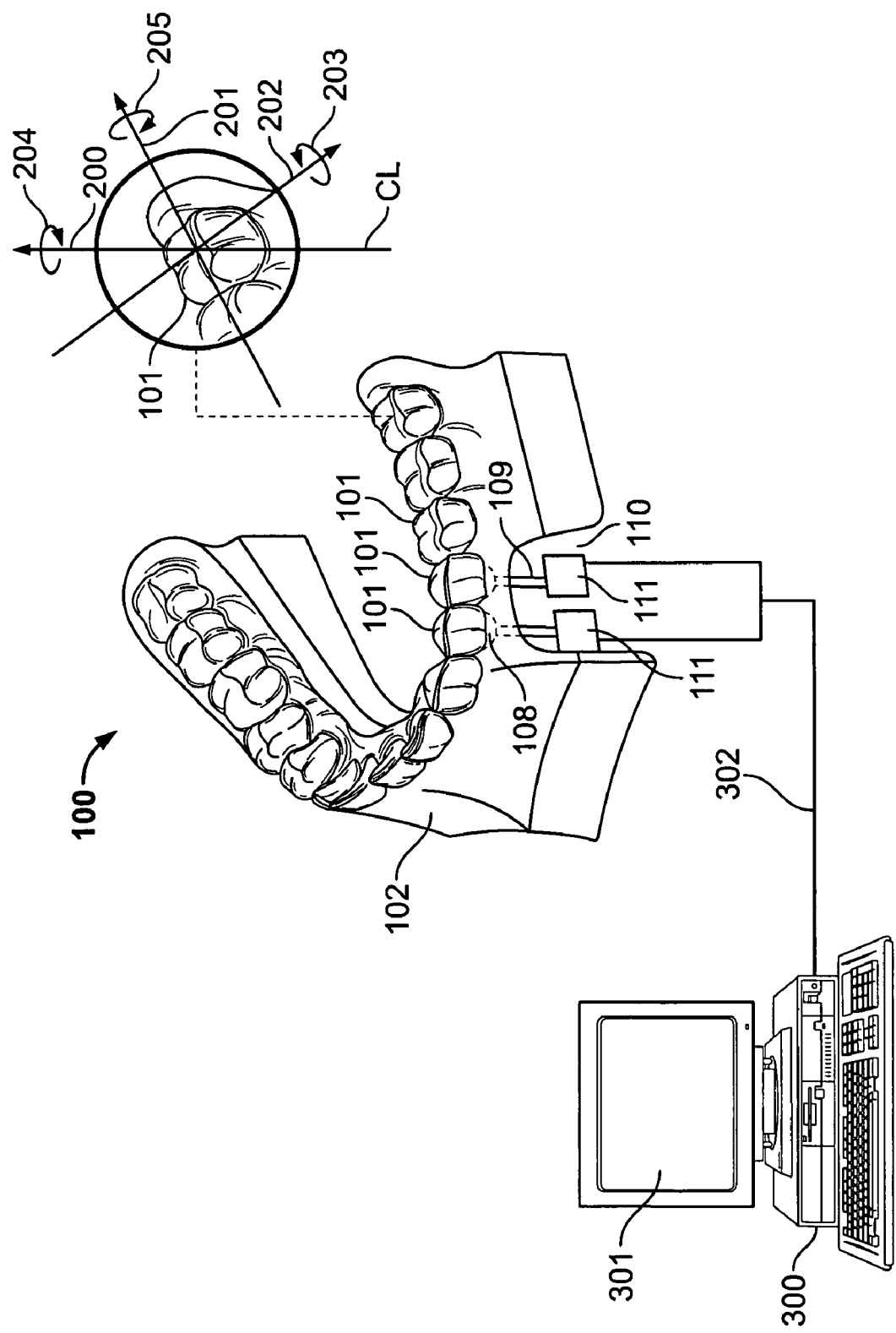
FIG. 6 is a simplified cut-away perspective view of the dental model system, revealing an embodiment of the manipulation devices, including View A which illustrates possible degrees of freedom in movement of each tooth member.

In a preferred embodiment, the ports 106 provide access to the inner portion 110 of frame 102, as shown in FIG. 6. The inner portion 110 houses one or more manipulation devices 111 which manipulate the tooth members 101. Once coupled to the manipulation devices 111, the tooth members 101 can be actuated and repositioned. The manipulation devices 111 are described in more detail below.

The simplified cut-away view of dental mold 100 shown in FIG. 6, reveals manipulation devices 111 disposed in the interior portion 110 of the frame 102. The manipulation device 111 can be a single mechanism, linked simultaneously to each individual tooth member 101 or group of members using, for example, a series of mechanical linkages or other similar means. However, as shown in FIG. 6, each tooth member 101 is preferably individually linked and controlled by a single manipulation device 111. Optionally, the tooth members 101 can be actuated by a combination of manipulation devices each providing some degree of manipulation within a given coordinate system.

To understand how tooth members 101 may be moved by a manipulation device 111, an arbitrary centerline CL is drawn through one of the tooth members 101, as seen in View A of FIG. 6. With reference to centerline CL, the tooth members 101 may be moved in the orthogonal directions represented by axes 200, 201, and 202 (where 200 is the centerline). A tooth member 101 may be translated along axes 201 and 202, or along any vector in the plane defined by these axes. Likewise, a tooth member 101 may be extruded or intruded by movement along axes 200. Torquing may be accomplished by rotation around axes 200, as represented by arrow 204. Rotation may also occur in the opposite direction than as indicated by arrow 204. Tipping or angulation may be achieved by rotation around axes 201 and 202, as represented by arrows 205 and 203 respectively. Similarly, rotation may also occur in the opposite direction than as indicated by these arrows. Thus, it is possible to perform movement of each tooth member 101 in six degrees of freedom (six DOF).

Accordingly, a practitioner can individually manipulate and arrange the tooth members 101 on the mold 100 to replicate a predetermined tooth arrangement. Each arrangement of the tooth members 101 may correspond to an incremental change in the configuration of the patient's teeth to provide a prescribed tooth movement required in each stage of an orthodontic treatment step.

The performance of six DOF movement usually requires a combination of components working individually and/or in unison to complete the various desired movements. In one exemplary embodiment, a tooth member 101 is coupled to a coupling member 109 at attachment section 108 at the bottom portion of the tooth member 101. Coupling member 109 is shown simplistically in FIG. 6 as a single member for illustrative purposes only. Since the coupling member 109 may need to provide multiple degrees of motion to tooth member 101, it may include many forms, shapes, and/or sizes. For example, certain movements may require that the coupling member 109 include one or a series of mechanical linkages, gears, springs, levers, hinges, cams, magnets and/or pneumatic pistons, used alone or in combination. The coupling member 109 couples the tooth member 101 to the manipulation device 111, also shown in a simplistic fashion merely for illustrative purposes and for generally understanding of placement.

Like the coupling member 109, the manipulation device 111 can be any single or combination of mechanical or electromechanical components that can be used to translate a driving force (electric or mechanical) into the directional movement of a member. For example, the manipulation device 111 may include a series of gears coupled to coupling member 109 and driven by a stepper motor. The motor receives a driving force, optionally from an external source, to drive the gears and incrementally rotate (i.e. arrows 203, 204, or 205) the coupling member 109, such that a degree of rotational movement is created in tooth member 101. Although, the actual mechanism used to provide the articulation of the tooth member 101 may comprise any number of interlinked components, it is likely that some of the components for providing such motion will be taken from the group comprising for example mechanical linkages, gears, springs, levers, hinges, cams, magnets and/or pneumatic pistons, used alone or in combination, as well as servos, solenoids, motors, electronics, solid state components, and the like. Alternatively, manipulation device 111 can be directly coupled to tooth member 101 without using intervening coupling member 109.

The manipulation devices 111, which create the actual six DOF movement of the tooth members 101, may be controlled manually and/or with the use of a microprocessor. In one embodiment, the repositioning of the individual tooth members 101 involves at least some of the components of manipulation device 111 being manually operated (non-computer aided). The manual controls may include, but are not limited to, knobs, screws, switches, joysticks, and other similar manual control mechanisms. In this embodiment, the practitioner will manually actuate each control mechanism, usually with finger pressure, which will in turn actuate the inner components of the manipulation device until a desired tooth arrangement is produced. Likewise, manual operation may be assisted with the visual aide of computer graphics or with instructions provided by software code.

In a preferred embodiment, the apparatus and methods of the present invention rely on the manipulation of manipulation devices 111 using a computer 300 or a workstation having a suitable graphical user interface (GUI) 301. In a specific example shown in FIG. 6, computer 300 is electrically coupled to manipulation device 111 to enable computer generated instructions to be sent to manipulation devices 111 via appropriate and well-known computer coupling methods, represented as line 302. The manipulation of tooth members 101 is driven using software appropriate for viewing and modifying the images (see above) on the GUI 301, as well as directing and controlling the tooth movements. Specific aspects of the controlling/directing software is described in detail hereinafter.

Figure 7:
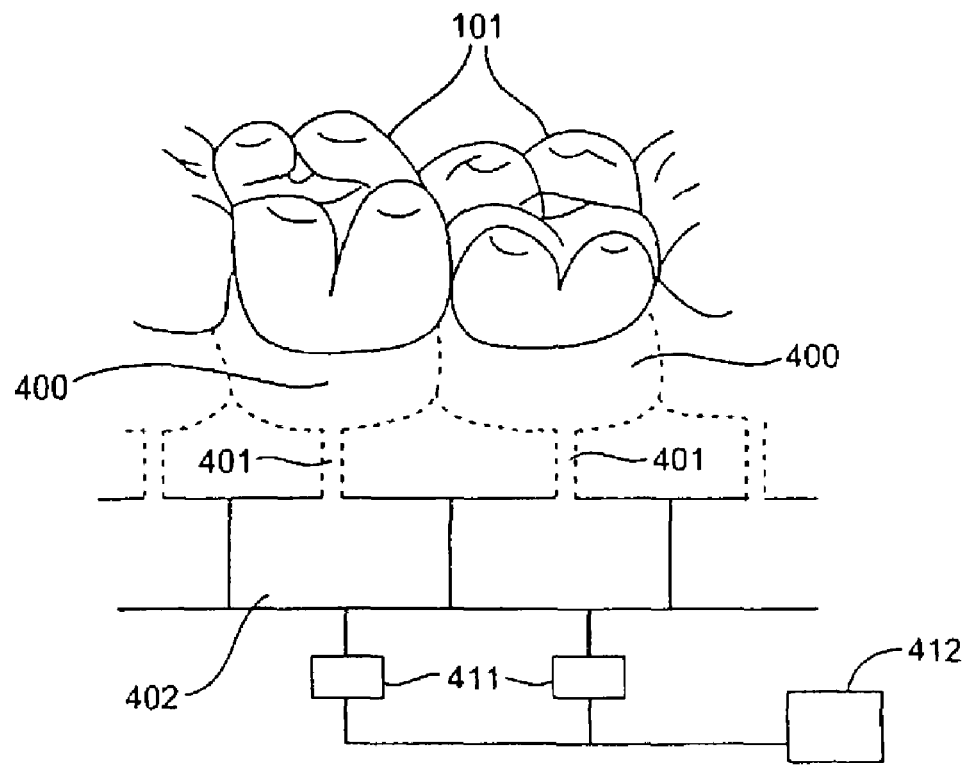
FIG. 7 illustrates an embodiment of manipulable simulated gingiva involving inflatable bladders.
Figure 8:
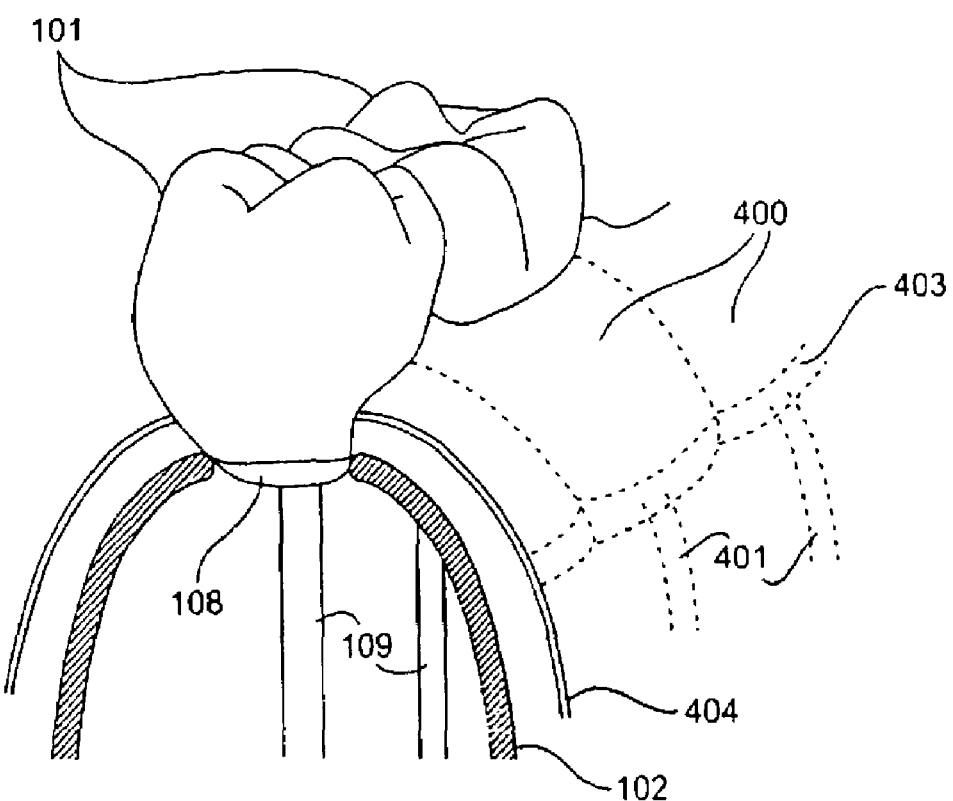
FIG. 8 is a cut-away perspective view of an embodiment of the inflatable bladders in relation to the tooth members and frame of the dental model system.
Figure 9:
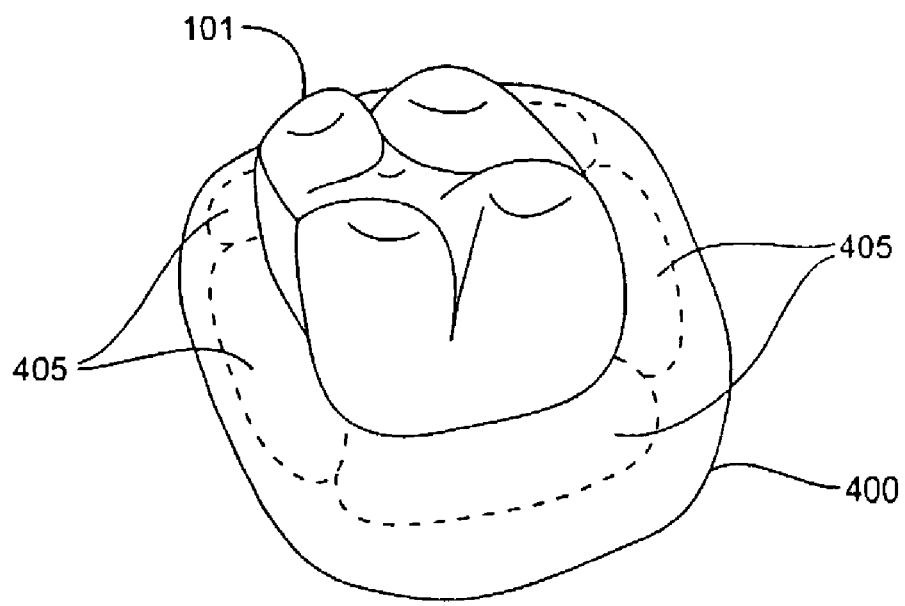
FIG. 9 illustrates an embodiment of sub-bladders within an inflatable bladder.

In a preferred embodiment of the present invention, the dental model system may be comprised of independently reconfigurable gingiva, in addition to tooth members, to model different tooth configurations with supporting simulated gingiva. One embodiment of reconfigurable simulated gingiva is schematically represented in FIGS. 7–9. Here, a series of inflatable bladders 400 surround each tooth member 101. As shown in FIG. 7, at least one bladder 400 is typically present to simulate the gingiva surrounding each tooth member 101. However, not depicted, each bladder 400 may simulate the gingiva surrounding more than one tooth member 101, or one continuous bladder 400 may simulate the gingiva surrounding all tooth members 101. The bladders 400 are comprised of an elastomeric material filled with air, liquid or a suitable medium. Each bladder 400 may have its own inflation port 401, leading to its own source 402. Therefore, each bladder 400 may be independently inflated and deflated by actuation of a control mechanism 411. Alternatively, the inflation ports 401 may be partially or wholly interconnected allowing manipulation of the bladders 401 with a reduced number or sources 402 or control mechanisms 411. Actuation of the control mechanism 411 may be manual or controlled by a digital processor 412.

Referring to FIG. 8, a simplified cut-away perspective view of the manipulable dental model system, reveals the possible placement of the inflatable bladders 400. The boundaries of the bladders 400 are represented by dashed lines 403. The bladders 400 may be located on the outside wall of the frame 102, which houses the attachment sections 108 and coupling members 109 which are linked to the tooth manipulation devices (not shown). Typically, the bladders 400 are covered by a continuous sheet 404 of elastomeric material to provide a smooth, consistent surface. However, the bladders 400 may alternatively be present without a cover.

Manipulation of the simulated gingiva may be further refined by a number of design features. First, each inflation bladder 400 may house a number of smaller sub-bladders 405, as shown in FIG. 9. The sub-bladders 405 may be inflated with air, liquid or a suitable medium which may or may not be the same as that which fills the main inflation bladder 400. Likewise, the sub-bladders 405 may be comprised of a material which may or may not be the same as the main inflation bladder 400. Differences in material and inflation medium may provide differing inflation dynamics. Second, each inflation bladder 400 may be comprised of a variable wall to provide differing inflation dynamics throughout the bladder 400. The wall may vary in thickness, material, amount of crosslinking of the material and number of layers, to name a few. Each variant may provide a different dynamic. For example, a portion of a bladder comprised of thin wall material will distend at a quicker rate than a portion of the bladder comprised of a thicker wall material. Thus, the simulated gingiva may be manipulated to replicate fine details of the patient's gingival configuration.

Figure 10:
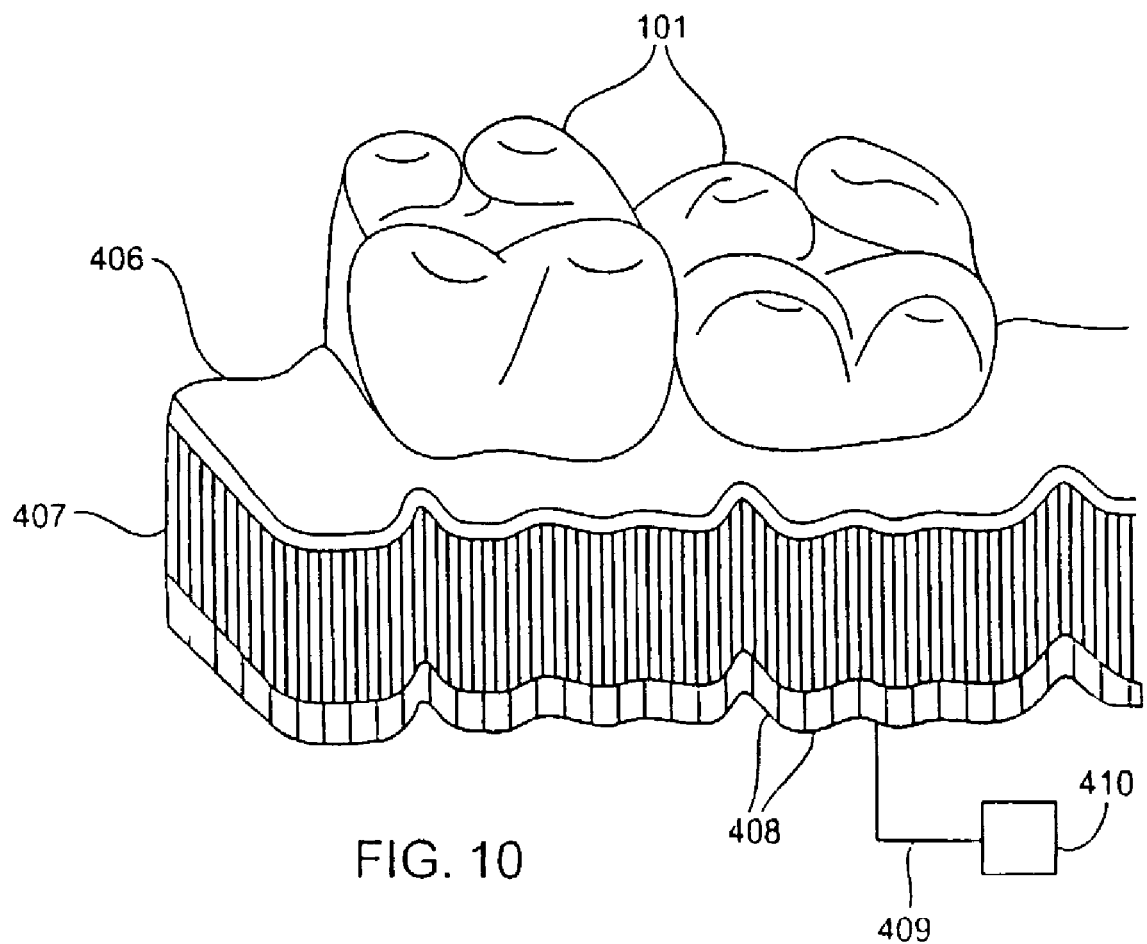
FIG. 10 is a perspective view of an embodiment of manipulable simulated gingiva involving movable support shafts.

Another embodiment of reconfigurable simulated gingiva is schematically represented in FIG. 10. Here, the simulated gingiva may be comprised of a flexible sheeting 406 of any suitable material, such as nylon, silicone, latex rubber, polyurethane, woven materials or cloth. Attached to the underside of the sheeting 406 may be a series of support shafts 407. The support shafts 407 may be of any cross-sectional geometry and dimension. The support shafts 407 may be manipulated individually or in groups by control mechanisms 408, similar in concept to the manipulation devices 111 used to manipulate the tooth members 101. Like the tooth members 101, the support shafts 407 may be manipulated in up to six degrees of freedom and the control mechanisms 408 may be electrically coupled 409 to a digital processor 410 for processor control.

Figure 11:
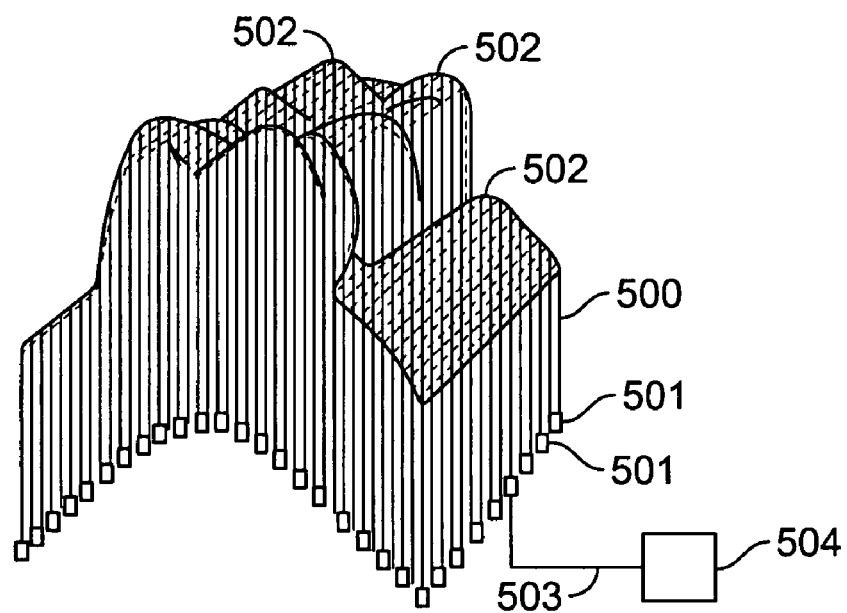
FIG. 11 is a perspective view of an embodiment of a reconfigurable dental model system comprised of movable model shafts.

Additional embodiments of the present invention involve alternative designs and methods of reconfiguring a single dental model system to model different tooth and gingiva configurations. Referring to FIG. 11, a single model system may be comprised or partially comprised of a series of model shafts 500. The model shafts 500 may be of any cross-sectional geometry and dimension, and they may have any tip design. The model shafts 500 may be manipulated individually or in groups in the vertical direction by one or more control mechanisms 501, represented by boxes. Upon actuation of the mechanisms 501, the model shafts 500 may be raised to varying levels. Together, the tips 502 of the shafts 500 may form the surface features of the tooth members, gingiva and other dental features. New configurations may be created by simply altering the tip levels by manipulating the model shafts 500. The model shafts 500 may be manipulated manually by the control mechanisms 501. Alternatively, the control mechanisms 501 may be electrically coupled 503 to a digital processor 504 for processor control.

Figure 12A:
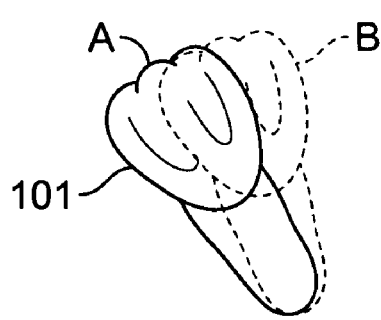
FIGS. 12A and 12B illustrate an embodiment of a method of reconfiguring a dental model system involving resurfacing.
Figure 12B:
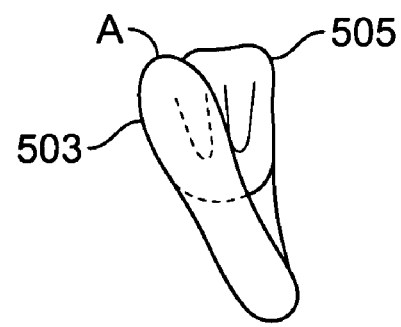

Referring now to FIGS. 12A and 12B, a single model system may be reconfigured to model different tooth and gingiva configurations by repeated resurfacing of the original mold. For example, as shown in FIG. 12A, it may be desirable to angulate a tooth member 101 from position A, represented by a solid line, to position B, represented by a dashed line, in the original mold. Rather than separating, angulating and recoupling the tooth member 101 to the mold, the tooth member 101 may remain in position A and be resurfaced. As shown in FIG. 12B, portions of the tooth member 101 may be removed, leaving a core 503, represented in black, in position A. A new material portion 505, represented in white, may be added to the right side to create the appearance that the tooth member 101 has moved to position B. Such resurfacing may be repeated to create different tooth and gingival configurations.

When using the reconfigurable dental mold 100 to produce a series of elastic positioning appliances 103 for orthodontic treatment, the mold 100 may be manipulated through a series of tooth configurations representing each stage in orthodontic treatment. As described previously, the initial tooth configuration is represented by the IDDS. This digital information is introduced to computer 300 for manipulation of the mold 100. The IDDS data serves as a baseline from which manipulation of the tooth members 101 begins. The Align Technology software (TREAT) described above, may be employed to determine the final tooth arrangement prescribed as the goal of the orthodontic treatment. Alternatively, the teeth may be virtually repositioned based on the visual appearance or instruction from the orthodontist. However, once the user is satisfied with the final arrangement of teeth, the final tooth arrangement is incorporated into a final digital data set (FDDS). Based on both the IDDS, FDDS, and optionally user input, a plurality of intermediate digital data sets (INTDDS's) are generated to correspond to successive intermediate tooth arrangements. The data sets are then reviewed by the orthodontist for accuracy.

In a preferred approach, the practitioner may direct the software to send an instruction to a manipulation device 111 to direct a tooth member 101 to move to a position which corresponds to a position digitally represented in the INTDDS and/or FDDS and visually represented on GUI 301. After the tooth members 101 are each manipulated and arranged to correspond to the INTDDS and/or to the FDDS data, the dental model system can be used to fabricate the system of incremental elastic positioning appliances 103 as described below.

Figure 13:
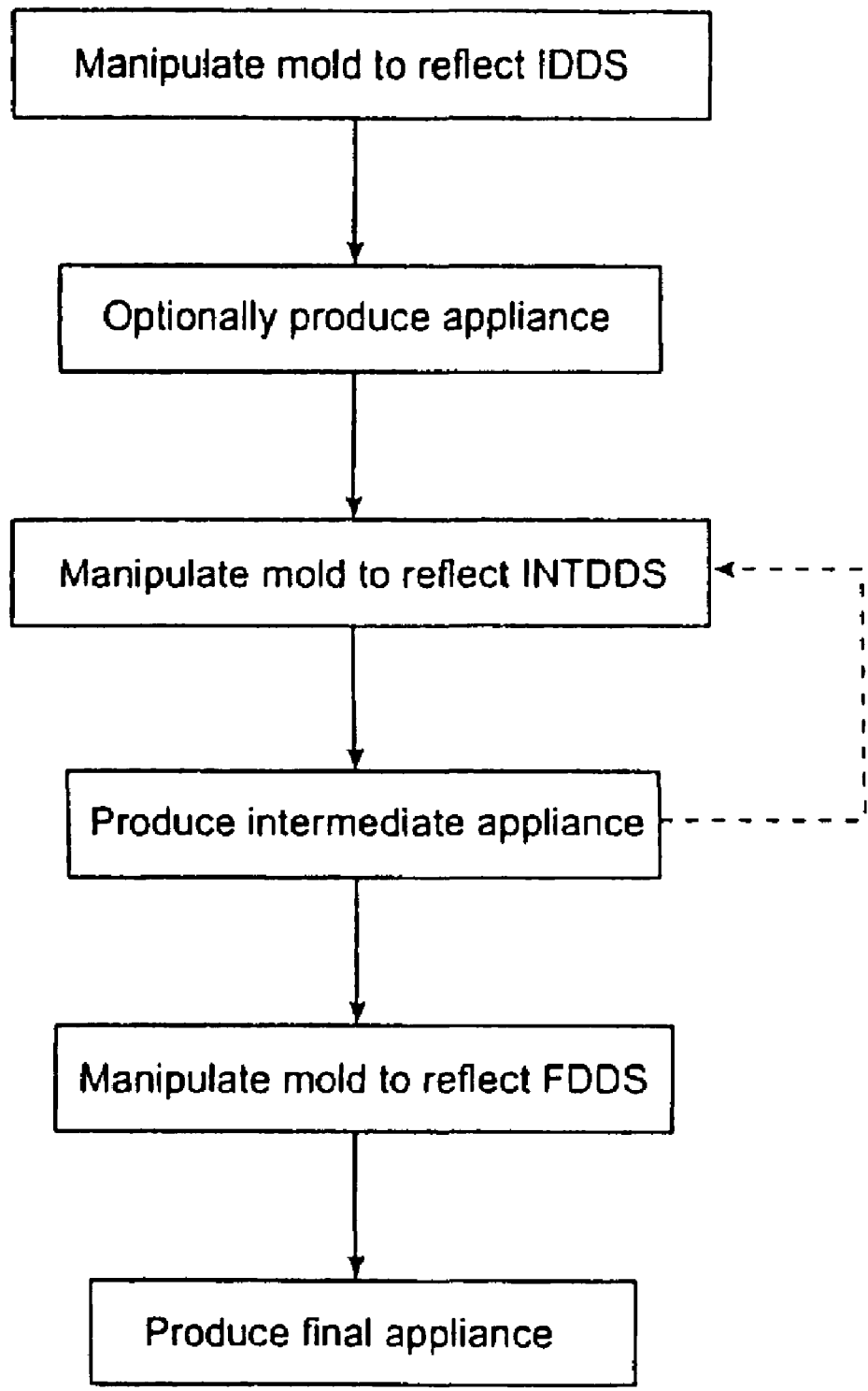
FIG. 13 is a flow diagram of a possible patient treatment method according to the principles of the present invention.

Referring now to FIG. 13, a flow diagram is shown describing an embodiment of a patient treatment method using a manipulable dental mold 100 and elastic positioning appliances 103 according to the principles of the present invention. At the outset of the orthodontic treatment method, the reconfigurable dental mold 100 is manipulated to reflect the initial tooth and gingiva arrangement described by the first digital data set (IDDS). An elastic positioning appliance or other appliances may be produced from the mold in this configuration. The mold 100 may then be manipulated to reflect the first intermediate tooth arrangement prescribed by the first intermediate digital data set (INTDDS). At this point, an elastic positioning appliance may be produced from the manipulable mold for the first stage of treatment in the progressive alignment series. Typically, such treatment involves a series of treatment stages. For each stage, the mold is manipulated to reflect the desired intermediate tooth configuration and a positioning appliance is produced. This is repeated for each INTDDS. Finally, the mold is manipulated to reflect the final tooth configuration prescribed by the final digital data set (FDDS), from which the final positioning appliance is produced. This appliance may be worn until the patient's dental features are properly aligned in the desired final arrangement, and it may be optionally worn thereafter to retain the teeth in the desired position.

The practitioner may choose to create configurations for a sufficient number of appliances at the outset of treatment which can provide the desired treatment goals (i.e. a final tooth arrangement), thus producing an initial set of appliances. For example, the practitioner may determine configurations at the outset for at least three appliances, but most likely more. Preferably the determination of the number of configurations and appliances created is dictated by the number of stages of treatment deemed necessary by the practitioner.

However, not all configurations and appliances need to be determined at the outset of treatment. A practitioner may choose to create from one to all appliances at the outset of treatment or the practitioner may wait and produce some appliances at a later time. Furthermore, it may be necessary to make appliances again at a later time to revise a configuration to redirect the treatment. To this end, the practitioner observes the patient at each stage of the treatment, to determine if a new configuration and appliance or set of configurations and appliances are needed to re-direct the treatment to reach the final tooth arrangement. If at any time after making an observation the practitioner determines that an appliance or set of appliances are not producing the desired intermediate tooth configuration, the practitioner can further determine an actual intermediate tooth configuration that can redirect the treatment. Subsequently, the practitioner determines the configurations that follow the newly determined actual intermediate arrangement for producing additional appliances for the re-directed treatment. In particular, once the practitioner decides that an initially determined set of treatment steps and appliances is not adequate, the practitioner can determine the actual intermediate tooth configuration that has been achieved, either by taking a mold or by direct scanning of the teeth, e.g. as described in U.S. Pat. No. 5,975,893, previously incorporated herein by reference. Once the intermediate configuration is known, subsequent successive movement steps can be calculated and appropriate positioning appliances planned, also as described in U.S. Pat. No. 5,975,893. A new set of appliances can then be produced and treatment resumed. In some cases, it might be appropriate to only partially plan the treatment at the outset with the intention of making a second (and perhaps third, fourth, or more) appliance at a time after the outset of treatment. The manipulable and reconfigurable dental model systems may optionally be used with the appliance planning protocols that rely on determining one or more actual intermediate tooth configurations during the course of a single treatment. The treatment cycle of observation of the intermediate configurations followed by either continuation to the successive configuration or modification of the treatment configuration can be repeated until the practitioner is satisfied that the final tooth arrangement has been achieved, at which time the treatment may end.

Figure 14:
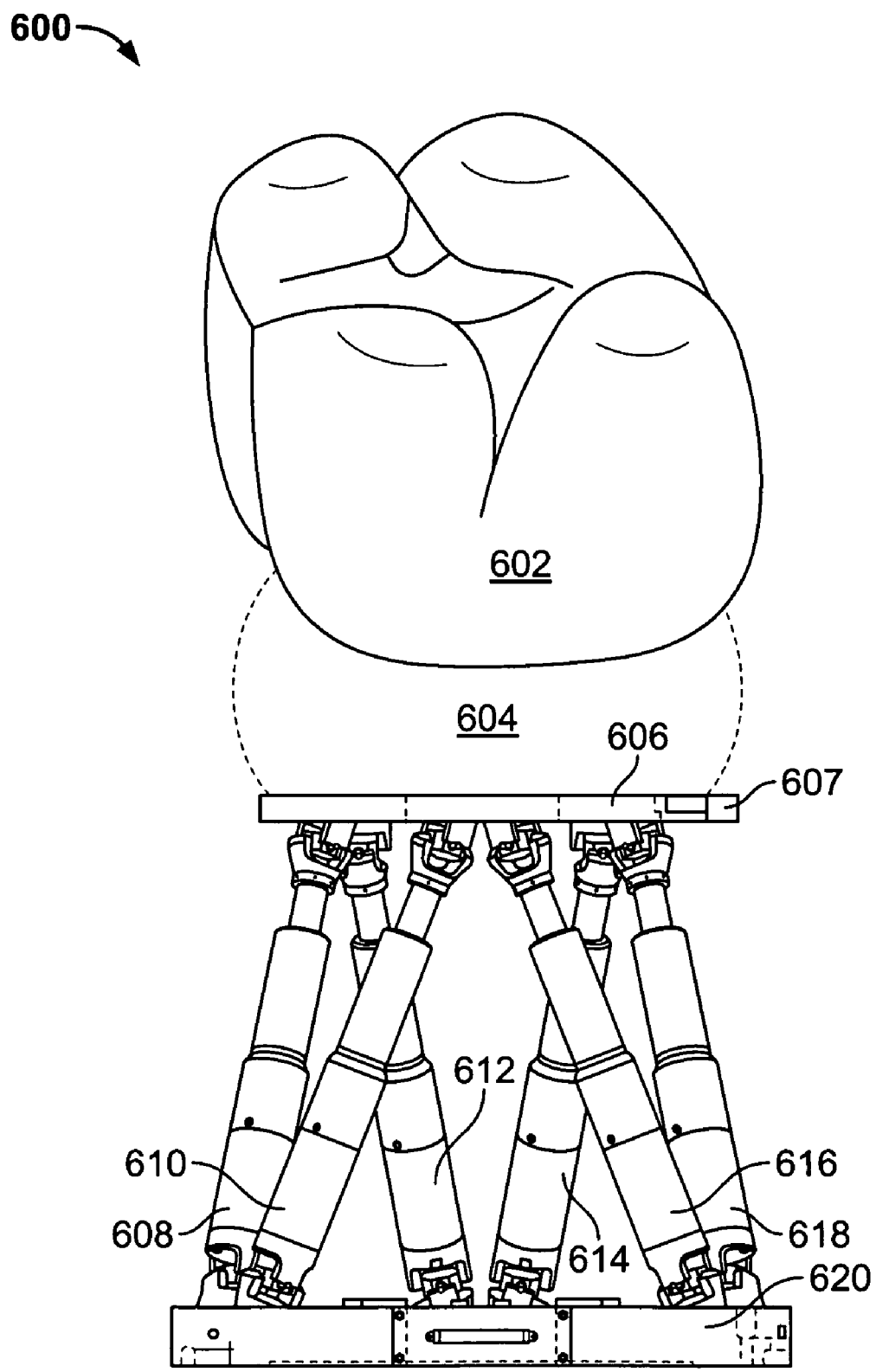
FIG. 14 is a perspective view of another embodiment of the reconfigurable dental model system.

Referring now to FIG. 14, another embodiment 600 of the manipulation device or positioner 111 is shown. In the embodiment of FIG. 14, positioner 600 is a micro-Stewart platform (hexapod) having six actuators or struts 608–618 to support/move a moveable platform 606. This is an arrangement of six variable length actuators that replace the sliding beams and rotating members of conventional orthogonal machines. The platform 606 supports a base 604 upon which a tooth member 602 rests. The actuators 608–618 rest above a fixed foundation 620. The actuators 608–618 are controlled by a computer to provide six degrees of freedom in movement. Suitable positioners include the M-5×1 series of MicroMotion Robot commercially available from Physik Instrumente (PI) GmbH & Co. KG in Karlsruhe/Palmbach, among other suppliers.

A sensor 607 is coupled to the platform 606 to provide positional feedback to the control computer. Alternatively, individual sensor may be provided on-axis with the actuator to provide precision measurement and control of the moving platform 606. The sensor is needed for feedback control, but may be omitted for open-loop applications in which calibration of the stage may be sufficient to characterize the stage motion, or when other types of feedback, such as vision, are used. Additionally, a safety stop may be included in the positioner and may be positioned on either side of each actuator. This prevents accidental damage to the actuator due to, for example, unintended contact between a robot and the moving stage. In case of accidental contact, only limited rotation about the flexure would occur before the safety stop halts the movement.

The tooth member 602 can be positioned above the base 604 using a suitable pick-and-place machine available from Philips or Siemens. The tooth member can be placed one at a time or in parallel (set).

In one embodiment, a physical model of the patient's teeth is obtained using suitable impression/mold technique. Teeth on the physical model are separated into individual tooth members using a CNC machine. The separated tooth members are then placed on a plurality of positioners 600. The positioners are then controlled or configured by the computer to position the tooth members into a dental mold configuration. At the outset of the orthodontic treatment method, the reconfigurable dental mold is manipulated to reflect the initial tooth and gingiva arrangement described by the IDDS. An elastic positioning appliance or other appliances may be produced from the mold in this configuration since the mold contains, in effect, positive tooth models of each successive stage of the treatment. After the positive models are prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the tradename BIOSTAR from Great Lakes Orthodontics, Ltd., Tonawanda, N.Y. 14150. The molding machine produces each of the appliances directly from the positive tooth model and the desired material. Suitable vacuum molding machines are available from Raintree Essix, Inc.

The mold may then be manipulated to reflect the first intermediate tooth arrangement prescribed by the first INTDDS. At this point, an elastic positioning appliance may be produced from the manipulable mold for the first stage of treatment in the progressive alignment series. Typically, such treatment involves a series of treatment stages. For each stage, the mold is manipulated to reflect the desired intermediate tooth configuration and a positioning appliance is produced. This is repeated for each INTDDS. Finally, the mold is manipulated to reflect the final tooth configuration prescribed by the FDDS, from which the final positioning appliance is produced. This appliance may be worn until the patient's dental features are properly aligned in the desired final arrangement, and it may be optionally worn thereafter to retain the teeth in the desired position.

In another embodiment, a physical model of the patient's teeth is obtained using suitable impression/mold technique. Teeth on the physical model are separated into individual tooth members using a CNC machine. Each separated tooth is moved by a pick and place machine or a 6-axis robot that selects the tooth and places the tooth on a fixed archform. An elastic positioning appliance or other appliances may be produced from the archform with the positioned teeth in this configuration since the archform with the thus positioned teeth is a positive model of each successive stage of the treatment. After the positive model is prepared, a conventional pressure or vacuum molding machine maybe used to produce the appliances. The pick and place machine or 6-axis robot then moves each tooth as appropriate for the next stage, and the next appliance can be produced. This process is repeated for all appliances.

In one embodiment, instead of making tooth members directly from an impression of the patient's teeth, an approximation can be used. In this embodiment, the patient's teeth are digitally scanned. Next, each of the patient's teeth is compared against a library of tooth members, and the closest tooth member is selected from the library as a proxy for the tooth. The selected tooth member is then placed on the base 604, and the next tooth is then evaluated. This process continues until all teeth have been placed on the frame.

The comparison of the patient's scanned teeth with the library of tooth member can be done using a number of features. For example, the library stores tooth members in accordance with the tooth type (molar, premolar, and incisor, among others). The shape, volume, and ridges of the tooth are used to identify the closest tooth having the same tooth type. Other basis for matching a tooth against a library of tooth members can be used.

An exemplary template teeth matching process is as follows:
1. All the teeth template will be indexed based on tooth types.
2. Mirror flag:
   a. True, take the template as is.
   b. False, take the mirror images of the geometry; the mirror axis will be defined later.
3. A unique coordinate system will be defined by the following:
   a. View from the buccal side, with up vector point from root to tip
   b. Z is defined as FACC tangent direction from the root to the tip
   c. X is the normal vector of FACC point on the crown surface
   d. Y is the perpendicular vector of FACC tangent
   e. The cross product X and Y get the Z
4. Certain unique measurement will define metrics for quick index keys:
   a. Length of FACC curve
   b. Tips
   c. Grove
   d. Tooth width
5. The match engine will first identify the index keys, the search template teeth database; find the subset of potential candidates based on least mean square method and acceptable threshold.
6. Then the match engine will go through each candidate selected above for further crown surface matching, see super impose patent for more details.
7. The overlapping area, which is defined as the distance within certain tolerance will be calculated.
8. The distance difference between tooth template and tooth within the overlapping area will be calculated; the tooth template with the smallest standard deviation will be selected. If the minimum standard deviation is above a certain limit, a certain warning will be given to indicate that there is no existing tooth template available.
9. The matching will also determine how to mount tooth template on the platform.

While the above is a complete description of the preferred embodiments of the invention, various alternatives, modifications, and equivalents may be used. Hence, an arrangement of several co-operating hexapods can be used to provide its high stiffness combined with simultaneous movement around 6 axes, for example. Moreover, although micro-actuators and struts have been discussed with reference to the hexapod or the Stewart platform, the micropositioner can also be a piezoelectric transducer such as lead zirconate titanate transducer (PZT). The PZT transducer responds to a voltage change by changing its length proportional to the PZT gain. PZT actuators consist of thin layers of electroactive ceramic material electrically connected in parallel and the total displacement is the sum of the displacements of the individual layers.

Other alternatives include having an array of pins that can be actuated to particular positions to form a predetermined 3D shape. The array of pins is actuated by a computer to form a positive model of a jaw at a particular treatment stage. The pressure or vacuum molding machine may be used to produce the appliances. Yet another alternative provides an array of air streams whose height is controlled in a manner similar to the actuated pins. The array of air streams form a virtual positive model of the jaw for each treatment stage and the molding machine can be used to produce the appliances. The array of pins or streams technique is advantageous in that no physical model is needed and the array can be reset for another stage without wasting material.

Other micro-actuators or positioners can be used as well. Therefore, the above description should not be taken as limiting the scope of the invention which is defined by the appended claims.

What is claimed is:

1. A dental appliance fabrication system, comprising:
   a reconfigurable dental model including a frame having one or more tooth members disposed on the frame; and
   one or more micro-positioners each respectively coupled to the one or more tooth members to move the tooth members in six degrees of freedom relative to the frame.

2. The system of claim 1, wherein said micro-positioner comprises a handle to allow an operator to manually position said tooth member in desired configurations.

3. The system of claim 1, further comprising a computer connected to deliver computer-generated instructions to said micro-positioner to position said tooth member in desired configurations.

4. The system of claim 1, further comprising an arch-shaped conveyor coupled to the one or more tooth members to position a different set of tooth members onto the frame.

5. The system of claim 1, further comprising a pick-and-place system to mount each tooth member on the frame.

6. The system of claim 1, further comprising a pick-and-place system to mount a set of tooth members on the frame in parallel.

7. The system of claim 1, wherein the micro-positioner comprises a Stewart platform or a hexapod.

8. The system of claim 1, wherein the micro-positioner further comprises:
   a movable platform; and
   a plurality of actuators attached to the movable platform.

9. The system of claim 8, further comprising a plurality of flexures configured to attach each of the plurality of actuators to the movable platform.

10. The system of claim 8, wherein the actuators are symmetrically attached about the movable platform.

11. The system of claim 1, further comprising a sensor configured to sense movement of the micro-positioner and a motion limiter configured to limit the movement of the micro-positioner.

12. The system of claim 1, wherein said frame is configured to represent a complete patient's dental arch.

13. The system as in claim 1, wherein the reconfigurable dental model further includes a simulated gingiva, wherein the tooth members extend through the gingiva to provide a model suitable for molding polymeric appliances thereover.

14. The system of claim 13, wherein the tooth members extend through ports in the gingiva having a variety of shapes, including rectangular, circular, multi-sided and/or multi-curved.

15. The system of claim 14, wherein the ports comprise a continuous channel along at least a portion of the gingiva.

16. The system of claim 13, further comprising one or more gingiva micro-positioners coupled to at least a portion of said simulated gingiva for reconfiguring said gingiva.

17. The system of claim 16, wherein the simulated gingiva comprises at least one inflatable bladder.

18. The system of claim 16, wherein the micro-positioner is manually controlled for inputting gingival position information.

19. The system of claim 18, further comprising a digital processor for inputting gingival position information and driving the control mechanisms.

20. The dental mold system of claim 16, wherein the simulated gingiva is comprised of:
    a flexible sheet; and
    a plurality of support shafts attached to at least a portion of said sheet;
    wherein the control mechanisms are coupled to at least some of said support shafts for moving said support shaft(s).

21. The system of claim 20, wherein the control mechanisms are manually controlled for inputting gingival position information.

22. The system of claim 20, wherein the control mechanism are connected to the computer for inputting gingival position information to the control mechanisms.

23. The system of claim 1, wherein said tooth members are comprised of a material selected from the group consisting of plaster, stone, acrylic, urethane, epoxy, plastics, wood, paper, metals, ceramics, and porcelain.

* * * * *